United States Patent [19]
Cerwin et al.

[11] Patent Number: 5,833,055
[45] Date of Patent: Nov. 10, 1998

[54] SURGICAL SUTURE PACKAGE WITH PEELABLE FOIL HEAT SEAL

[75] Inventors: Robert J. Cerwin, Pipersville, Pa.; Clifford A. Dey; John M. Findlay, both of San Angelo, Tex.; Konstantin K. Ivanov, Bound Brook, N.J.; Robert Nuñez, Asbury, N.J.; Donald Pompei, Montville, N.J.; William R. Reinhardt, Belle Mead, N.J.; Mehmet Reyhan, E. Windsor, N.J.; David A. Szabo, Branchburg, N.J.

[73] Assignee: Ethicon, Inc., Summerville, N.J.

[21] Appl. No.: 623,874

[22] Filed: Mar. 29, 1996

[51] Int. Cl.⁶ .................................................. A61B 17/06
[52] U.S. Cl. ...................... 206/63.3; 206/227; 206/380; 383/211
[58] Field of Search ................... 206/63.3, 63.5, 206/227, 380, 388; 383/210, 211

[56] References Cited

U.S. PATENT DOCUMENTS

| | | | |
|---|---|---|---|
| 3,162,307 | 12/1964 | Regan, Jr. | 206/63.3 |
| 3,163,228 | 12/1964 | Arvidsson | 206/63.3 |
| 3,256,981 | 6/1966 | Kurtz | 206/63.3 |
| 4,961,498 | 10/1990 | Kalinski et al. | 206/63.3 |
| 4,967,902 | 11/1990 | Sobel et al. | 206/63.3 |
| 5,048,678 | 9/1991 | Chambers | 206/63.3 |
| 5,129,511 | 7/1992 | Brown et al. | 206/63.3 |
| 5,220,769 | 6/1993 | Brown et al. | 53/453 |
| 5,284,240 | 2/1994 | Alpern et al. | 206/63.3 |
| 5,341,922 | 8/1994 | Cerwin et al. | 206/63.3 |
| 5,439,102 | 8/1995 | Brown et al. | 206/63.3 |

*Primary Examiner*—Jimmy G. Foster
*Attorney, Agent, or Firm*—Herbert J. Hammond; Peter J. Thoma

[57] ABSTRACT

A package for maintaining a needle-suture product in a sterile condition includes a peelable foil container in which a peripheral heat seal defines a cavity for retaining a suture packet. The packet has a plastic tray and a stiff paper lid secured to the tray by hinged paper cleats extending into sockets in the tray. The lid covers most of the area of the tray, leaving an uncovered portion for accessing a needle mounted in the tray. A suture attached to the needle is coiled in a peripheral track in the tray so that an extended length of suture material can be retained in a relatively small space. The container has top and bottom aluminum foils with differentiated polymeric coatings on their interior surfaces, which are thermally fused to form the seal. Unsealed foil flaps are provided at one end of the container to enable peeling apart the foils to open the package.

20 Claims, 6 Drawing Sheets

SURGICAL SUTURE PACKAGE WITH PEELABLE FOIL HEAT SEAL

CROSS-REFERENCE TO RELATED APPLICATIONS

This application is related to two commonly-assigned patent applications filed in the U.S. Patent and Trademark Office on the same day as this application, the first such application being entitled "Apparatus for Feeding Foil Stock in a Process for Making Sealed Sterile Packages" (Attorney Docket No. 40752.09851) Ser. No. 08/624,926, pending, and the second such application being entitled "Method for Making Sterile Suture Packages" (Attorney Docket No. 40752.09858) Ser. No. 08/624,971, U.S. Pat. No. 5,623,810, the disclosures of each of such applications being incorporated herein by reference.

BACKGROUND OF THE INVENTION

1. Field of the Invention

The present invention relates to packages for surgical products, and more particularly to a sterile package for a needle-suture assembly.

2. Description of the Prior Art

Examples of prior art packages for surgical sutures are disclosed in U.S. Pat. Nos. 5,129,511; 5,220,769; 5,284,240; 5,341,922 and 5,439,102. A peelable foil suture package over which the present invention is an improvement is disclosed in U.S. Pat. No. 5,341,922, the disclosure of which is hereby incorporated by reference. Another prior art package manufactured by Ethicon, Inc. and widely used for many years is described herein in conjunction with FIGS. 1–7.

Figure 1:
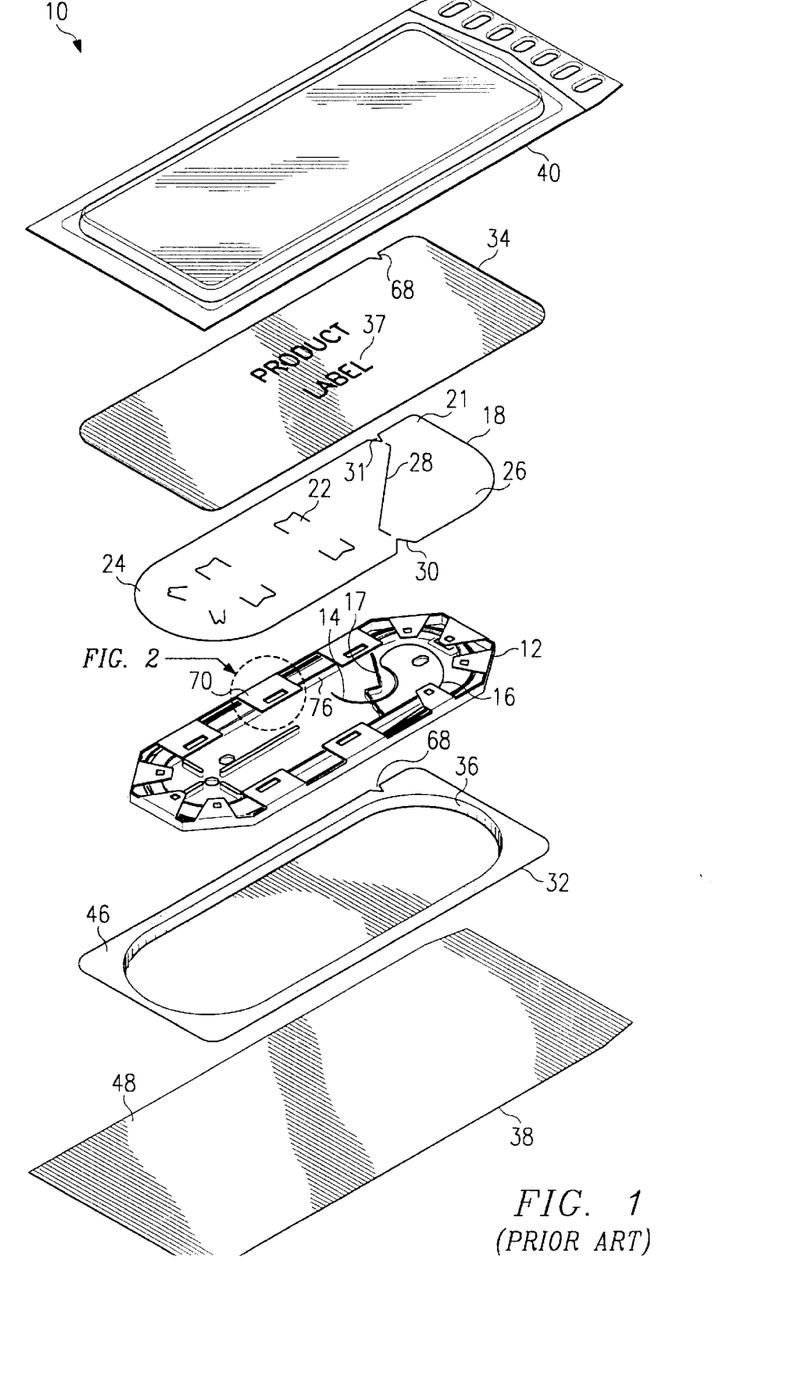
FIG. 1 is an exploded perspective view of a prior art package containing a needle-suture assembly.

Referring to FIG. 1, a prior art package for a needle-suture assembly as provided to the user is shown in an exploded perspective view and designated generally by reference numeral 10. The package 10 includes a generally oval-shaped tray 12 for retaining a needle-suture assembly consisting of a needle 14 and a suture 16. The suture 16 is attached to the needle 14 in a well known manner, such as by insertion of the end of the suture into an opening or channel in the end of the needle, and then crimping or swaging the end of the needle to tightly secure the suture thereto. The needle is held in place by a slotted rib 17 disposed on a flat interior surface of the tray 12. This feature is seen more clearly in FIG. 3. The suture 16 is coiled and lays in a track at the periphery of the tray 12 to enable an extended length of suture material to be retained in a relatively small space. For example, a conventional tray which measures 1 3/16 inches in width and 3 3/8 inches in length easily accommodates a two-foot length of suture material.

A paper lid 18 of substantially the same oval shape as the plastic tray 12, is attached to the top of the tray to form a packet 20. Extending beyond the generally oval-shaped outline of the tray 12 is a tear tab 21, which is located, as seen in FIG. 1, at one corner of the paper lid 18. As described in greater detail below, the tear tab 21 is used in opening the packet 20 to access the needle-suture assembly 14, 16. The lid 18 is attached to the tray 12 using interior tabs, a representative one of which is designated by reference numeral 22.

The paper lid 18 has a major portion 24 and a minor portion 26 separated by a tear line 28. V-shaped cutouts 30 and 31 are provided on opposite sides of the paper lid 18 near the ends of the tear line 28. The tear line 28 and cutouts 30 and 31 facilitate tearing the minor lid portion 26 away from the major lid portion 24 when opening the packet 20.

The suture packet 20, with the lid 18 attached to the tray 12 and containing the needle-suture assembly, is sealed in a sterile condition inside a container consisting of a bottom foil 32 and a top foil 34. The bottom foil 32 has an oval-shaped cavity 36 slightly larger than the suture packet 20 to receive and snugly retain the packet 20 within the cavity 26. The material of the container 32, 34 is an aluminum foil. Product label indicia 37 is printed on the top surface of the top foil 34.

Figure 6:
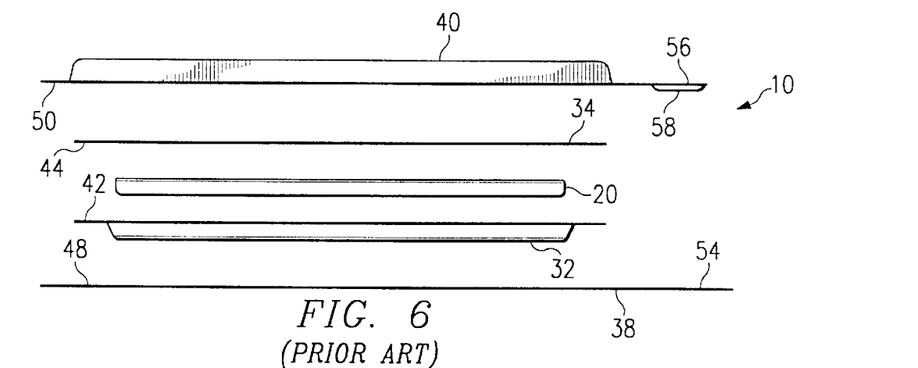
FIG. 6 is an exploded side view of the prior art package.

An overwrap consisting of a bottom sheet 38 and a top cover 40 completes the package 10. As depicted in FIG. 6, the suture packet 20 is loaded into the foil container 32, 34, which is later packaged inside the overwrap 38, 40, thus providing a redundantly sealed final product.

A polymeric seal coating is applied to the top surface 42 of the bottom foil 32 and the bottom surface 44 of the top foil 34. These identical coatings are selectively heated using a die (not shown) to cause them to melt together and form a peripheral seal around the cavity 36 to maintain the suture packet 20 in a sterile condition. As seen in FIG. 1, the peripheral seal resides entirely in the area which defines a flat shelf 46 which surrounds the cavity 36 in the bottom foil 32.

The bottom sheet 38 of the overwrap is a synthetic fibrous material commonly sold as Tyvek (a registered trademark of DuPont). The sheet 38 has a smooth top surface 48 which facilitates adhesive bonding with the cover 40. The cover 40 of the overwrap is a clear plastic material having an adhesive on a peripheral portion of the bottom surface 50.

Figure 7:
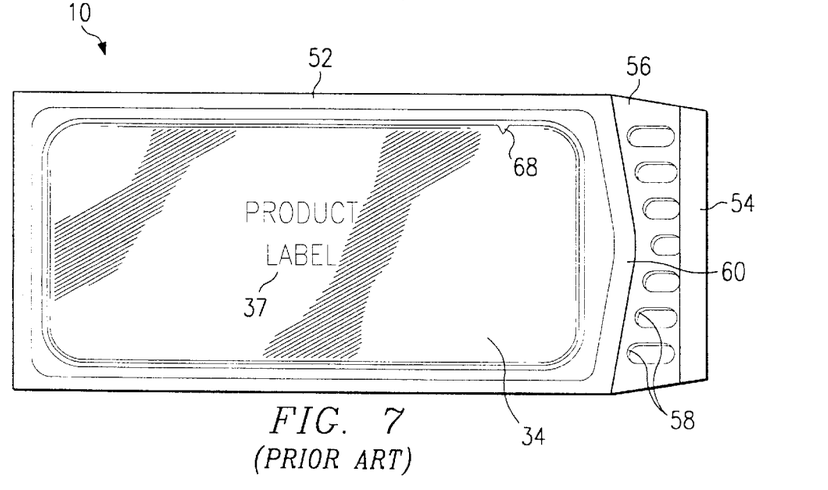
FIG. 7 is a top plan view of the prior art package.

FIG. 7 is a top view of the assembled package 10 in which the product label indicia 37 on the top surface of the foil container can be seen through the clear plastic of the overwrap cover 40. The adhesive on the bottom surface of the cover 40 forms a peripheral seal 52, shown lightly shaded.

Flaps 54 and 56 extend out to the right in the orientation of FIGS. 6 and 7 to facilitate opening the overwrap 38, 40. The flap 54 on the bottom sheet 38 extends slightly beyond the end of the flap 56 on the cover 40. Bubble-like depressions 58 are provided in the plastic cover 40 at the end of the flap 56 to facilitate peeling the flaps apart when opening the overwrap 38, 40. These bubbles 58 reduce the tendency of the flaps 54 and 56 to stick together. Also, the adhesive seal 52 has an apex-shaped portion 60 just to the left of the bubbles 58 to further facilitate peeling the flaps apart. The force required to begin tearing the adhesive seal 52 open is reduced by the apex-shaped portion 60 compared to a straight line adhesive seal in the flap area.

Once the overwrap 38, 40 has been opened, the foil container 32, 24 can be removed and opened to access the suture product protectively sealed within. This is facilitated by a V-shaped notch 68 in the edge of the container. The notch 68 is formed in a blanking operation in which a plurality of containers are separated from a frame following sterilization and sealing. The standard frame used in the prior art procedure consists of ten containers in two rows of five each. The notch 68 corresponds in location to the V-shaped cutout 31 in the paper lid 18, as seen in FIG. 1. The notch 68 extends only about 1/16 inch from the edge of the container inward so that it does not threaten the integrity of the seal. The width of the seal, as measured by the lateral dimension of the shelf 46, is about 1/4 inch.

Figure 2:
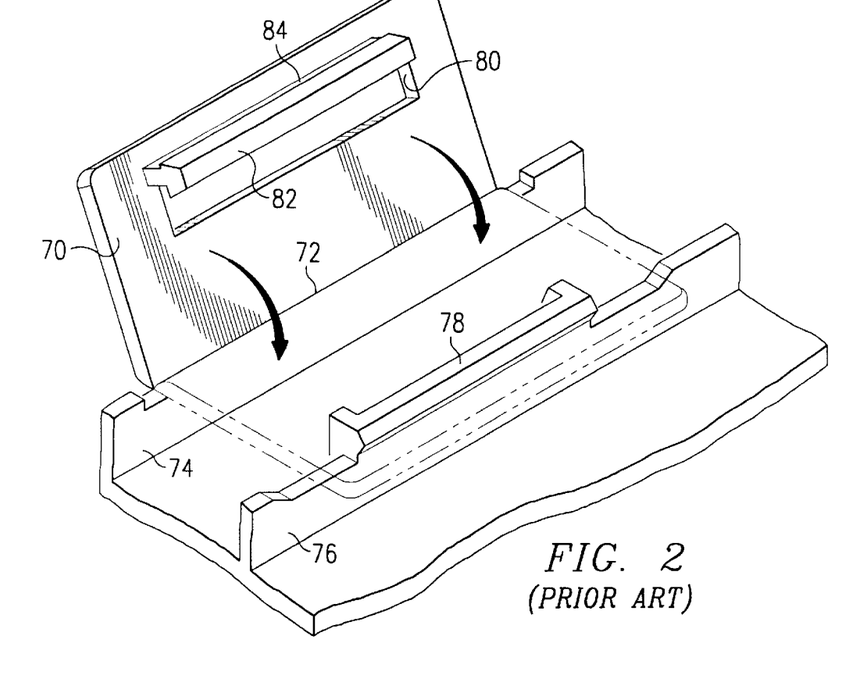
FIG. 2 is an enlarged perspective view of a portion of a suture packet of the prior art package of FIG. 1.
Figure 3:
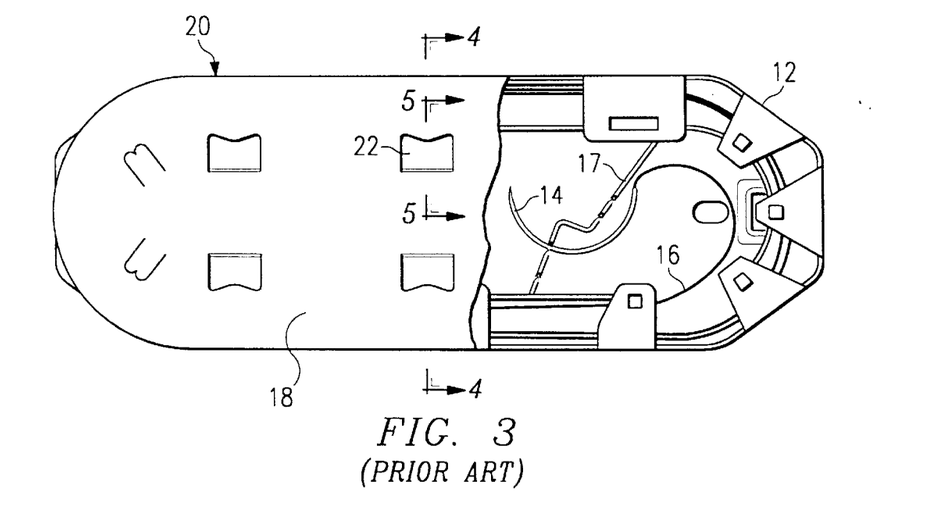
FIG. 3 is a top plan view of the prior art suture packet with a portion of a lid broken away to reveal a needle mounting area.

With reference to FIGS. 1 and 2, the technique for retaining the suture 16 in place in the packet 20 will be described. The tray 12 has a plurality of doors around the periphery, a representative one of which is designated by reference numeral 70. The door 70 is shown in the open position in FIG. 2 with phantom lines indicating the closed position. The door 70 is integrally formed with the plastic tray 12 and has a thin connection thereto to define a hinge 72. The hinge 72 lies along a vertical peripheral wall 74 of the tray 12. An oval-shaped inner wall 76 is spaced from the peripheral wall 74 to define a track within which the suture 16 rests in a coiled arrangement. Atop the inner track wall 76 is a clasp 78 which extends through a window 80 in the door 70 when the door is closed. Along the outer edge of the door 70 on the bottom surface is a pointed catch 82 which snaps in place under the edge of the clasp 78 when the door 70 is closed.

Figure 4:
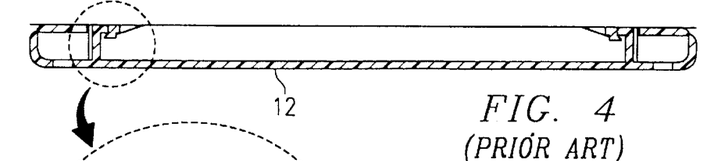
FIG. 4 is a lateral cross section taken through the center of the prior art packet of FIG. 3.
Figure 5:
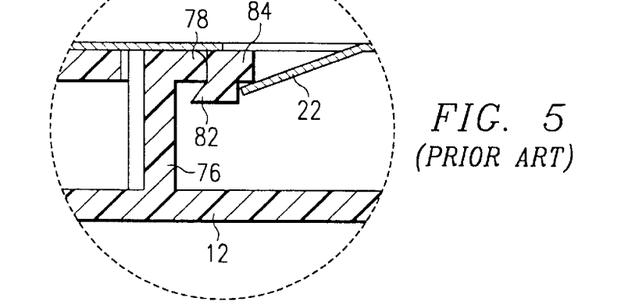
FIG. 5 is an enlarged view of a portion of the cross section of FIG. 4.

The manner in which the point of the catch 82 snaps in place under the edge of the clasp 78 is shown in cross section in FIGS. 4 and 5. As seen best in the enlarged view of FIG. 5, the outer edge of the door 70 defines a lip 84 which serves to secure the paper lid 18 to the tray. This is accomplished by depressing each of the several paper tabs 22 to snap into place in the manner shown in FIG. 5. The end of the paper tab 22 lies under the lip 84. The paper material of the lid 18 has sufficient thickness and resiliency so that the several tabs 22 will hold the lid in place atop the tray 12. However, it has been found in practice that there is a tendency for lids secured in this manner to be dislodged from their trays during manufacturing, thus causing downtime and related inefficiencies. This problem is addressed and solved by the improved package of the present invention described below.

The user accesses the suture product within the package 10 as follows. First, the overwrap 38, 40 is opened by pulling apart the flaps 54 and 56 and breaking the adhesive seal 52. The sealed container 32, 34 is then removed and torn open starting at the V-shaped notch 68. The minor portion of the lid 18 is torn away in the same tearing motion because the tear tab 21 is secured in the adjacent corner seal area of the container 32, 34. Once the package 10 has been torn open in this manner, the needle 14 can be accessed using conventional surgical forceps (not shown). The needle 14 and attached suture 16 can then be removed, the suture simply uncoiling as it is pulled out of the tray 12.

Development of the improved surgical suture package described herein arose from the desire to increase manufacturing efficiencies and simplify the user's task of opening the package to access the sterile needle-suture assembly contained therein.

SUMMARY OF THE INVENTION

In accordance with the present invention, an improved surgical suture package is provided for maintaining a needle-suture assembly in a sterile condition prior to its use in surgery. The improved package includes a sealed container having a cavity within which a suture packet is retained. The needle-suture assembly is mounted in the packet in a manner which enables an extended length of suture to be confined in a relatively small space. The container has top and bottom foils which are sealed together by thermally fusing heat-sensitive coatings to form a peripheral seal around the cavity. Specially adapted foil flaps are provided at one end of the container to enable the foils to be peeled apart to break the seal and permit access to the suture packet. The heat-sensitive coatings are specially adapted to facilitate peeling apart the foils.

An important feature of the present invention is the provision of a peelable foil heat seal in the package which encapsulates the sterile suture product. The presently preferred way of carrying out the invention is described in detail below with reference to FIGS. 8–17 of the accompanying drawings.

DETAILED DESCRIPTION OF THE INVENTION

Figures 8, 9:
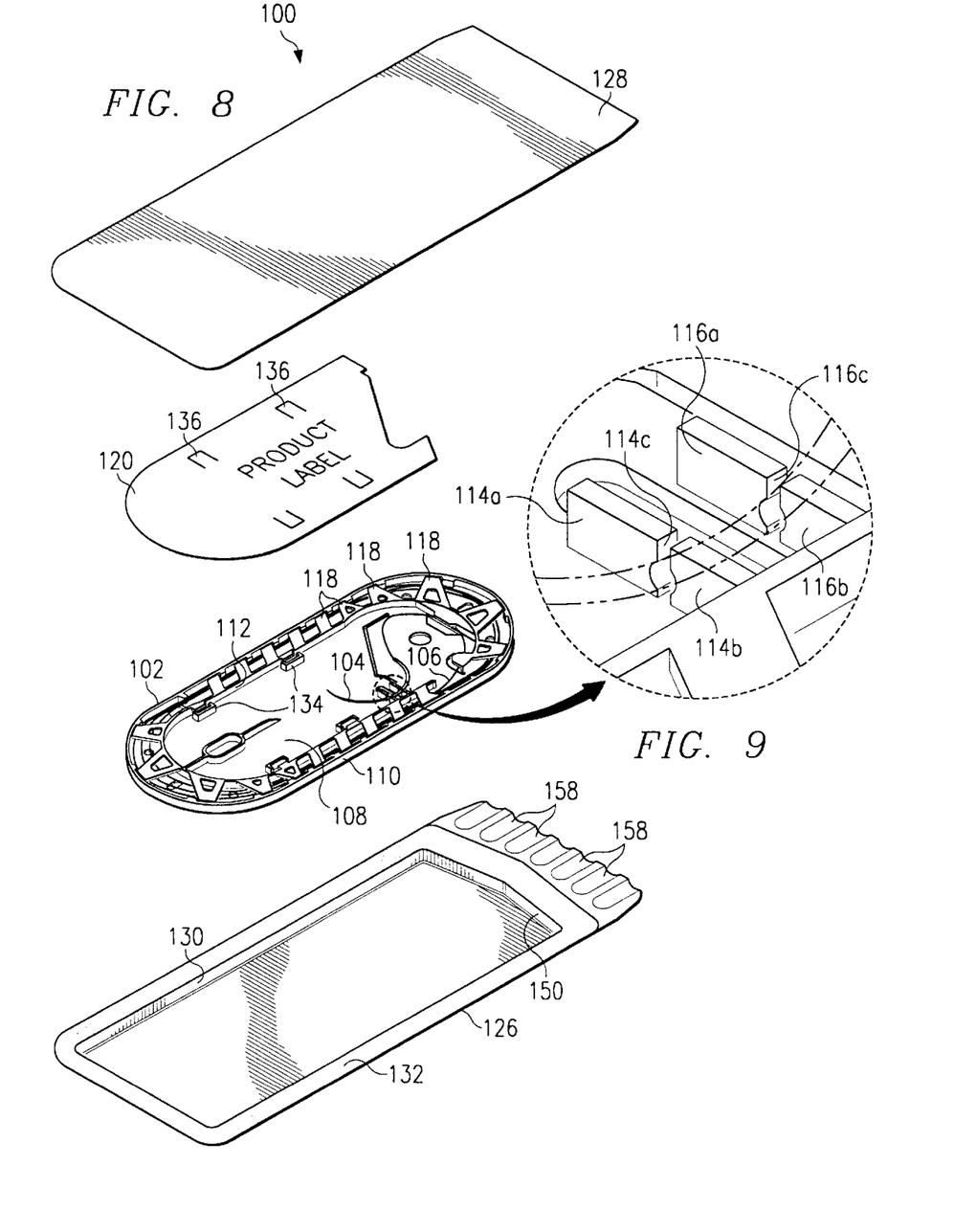
FIG. 8 is an exploded perspective view of a surgical suture package in accordance with the present invention.
FIG. 9 is an enlarged view of a portion of a tray showing the preferred manner for retaining a needle (shown in phantom lines) in place in the tray.

A preferred embodiment of the invention will now be described with reference to FIGS. 8–17. With particular reference to FIG. 8, an improved package for a needle-suture assembly is shown in an exploded perspective view and designated generally by reference numeral 100. The package 100 includes an oval-shaped tray 102 for retaining a needle-suture assembly consisting of a needle 104 and a suture 106. The suture 106 is attached to the needle 104 in a well known manner, such as by insertion of the end of the suture into an opening or channel in the end of the needle, and then crimping or swaging the end of the needle to tightly secure the suture thereto.

The tray 102 has a substantially flat base 108, an outer wall 110 extending upward around the periphery of the base, and an inner wall 112 extending upward from the upper surface of the base. The inner wall 112 is spaced inwardly from the outer wall 110 to define a track for retaining the suture 106 in a coiled arrangement at the periphery of the tray 102.

The needle 104 is held in place by slotted ribs extending up from the upper surface of the base 108. As seen more clearly in the enlarged view of FIG. 9, two adjacent parallel ribs are shown with a first rib consisting of rib elements 114a and 114b, and a second rib consisting of rib elements 116a and 116b. The rib elements 114a and 114b define a slot designated by numeral 114c in FIG. 9. Likewise, rib elements 116a and 116b define a slot 116c therebetween. The slots 114c and 116c have rounded inner surfaces shaped to conform to a needle, as shown in phantom in FIG. 9. Thus, a needle will be resiliently held in place by the ribs once it is pressed into a nesting position in the slots 114c and 116c.

Referring again to FIG. 8, the coiled suture 106 is retained in the peripheral track by zipper-like teeth, representative ones of which are designated by reference numeral 118. An automated procedure is preferably used to load the suture 106 into the tray 102. In operation, the teeth 118 are bent upwards, the suture is loaded in a coiled arrangement into the track defined by the walls 110 and 112, and then the teeth are allowed to resiliently return to the position shown in FIG. 8 to retain the coiled suture 106 in place in the peripheral track.

Figure 10:
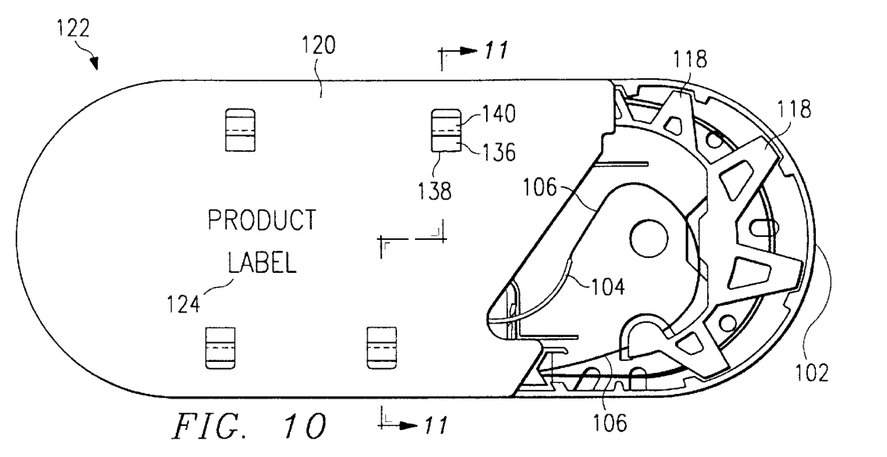
FIG. 10 is a top plan view of a suture packet in accordance with the present invention.

After the needle-suture assembly 104, 106 is in place in the plastic tray 102, a flat lid 120 is attached to the tray in the manner shown in FIG. 10. The tray 102 with the attached lid 120 is referred to as a suture packet, which is designated generally by reference numeral 122. The lid 120 preferably comprises a relatively stiff paper which is 0.012 inch thick. Product label indicia 124 is printed on the outer surface. The lid 120 preferably covers only a portion of the tray 102 including the portion within which the point of the needle 104 resides. The end of the needle 104 which is attached to the suture is exposed and readily accessible using conventional surgical forceps. Thus, once the package 100 has been opened, the user can easily grasp the needle 104 with forceps, pull it free from its slotted mounting and extract the entire length of suture 106 in a single motion. This can be accomplished without removing the lid 120.

Referring again to FIG. 8, the suture packet 122 is loaded into a container consisting of a bottom foil 126 and a top foil 128, which preferably comprise aluminum, each having a thickness of 1.5 mil. The bottom foil 126 has an elongated cavity 130 for receiving the suture packet 122. Surrounding the cavity 130 is a flange 132, the upper surface of which is used to form a seal with the bottom surface of the top foil 128. Heat sensitive coatings, described more completely below, are disposed on the sealing surfaces of the foils 126 and 128 to maintain the needle-suture assembly in a sterile condition within the package 100.

In manufacturing, the suture packet 122 is loaded into the bottom foil 126, the top foil 128 is placed on the bottom foil, and then a tacking operation is performed in which the seal coatings are selectively heated at several discrete points to hold the foils together during subsequent processing steps. At this stage of the procedure it is preferred to handle eight containers interconnected together in a two-by-four frame (not shown). The frame of eight containers is sent through a sterilization procedure. At the end of the sterilization procedure, a complete peripheral seal is formed around each cavity 130 to assure that the needle-suture assembly 104, 106 therein remains sterile until the individual package 100 is opened by the user. At the final stage of the manufacturing procedure, each frame is cut into eight individual packages.

The improved package 100 was designed to have approximately the same width and length as the prior art package 10 described above, which dimensions are approximately 2¼ inches by 5⅛ inches. It will be appreciated that the container 126, 128 of FIG. 8 is larger than the container 32, 34 of FIG. 1. Thus, the cavity 130 of the improved package 100 may be made larger than the cavity 36 of the prior art package 10.

Preferably, the larger cavity 130 is sized to accommodate suture packet 122 having the preferred dimensions of 1½ inches in width and 3¾ inches in length.

Figure 11:
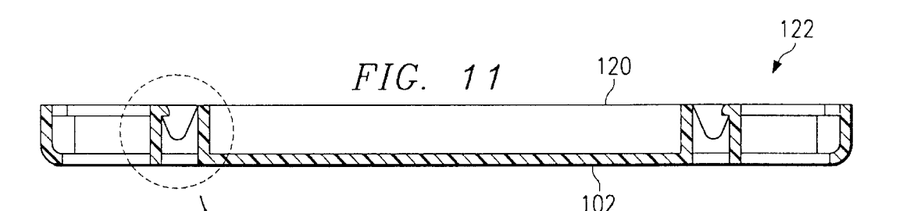
FIG. 11 is a cross section of the packet of FIG. 10 taken along staggered line 11—11 of FIG. 10.

Now referring to FIGS. 10–12, a preferred technique for attaching the paper lid 120 to the tray 102 will be described. As seen in FIG. 10, the lid 120 covers a major portion of the tray 102 including the portion within which the point of the needle 104 resides. The lid 120 has four points of connection to the tray 102, two of which are seen in cross section in FIG. 11. As seen best in the enlarged view of FIG. 12, a socket 134 receives a folded tab 136 which is formed by a three-sided cutout of the lid 120. Four like sockets 134 can be seen in FIG. 8 disposed on the upper surface of the tray 102. Four tabs 136 are also seen in FIG. 8 in their original pre-folded condition in the lid 120.

Figure 12:
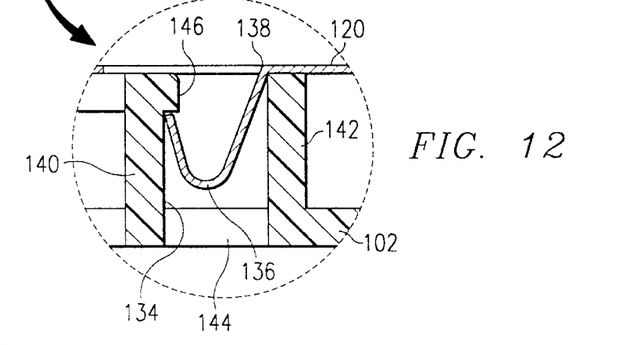
FIG. 12 is an enlarged view of a portion of the cross section of FIG. 11.

Referring to FIG. 12, each tab 136 is connected along one edge 138 to the paper lid 120, thereby providing a hinge for movement of the tab 136 down into the socket 134. The socket 134 comprises walls whose interior surfaces define an opening. In particular, a first wall 140 is parallel to and faces a second wall 142. The first wall 140 is preferably a portion of the inner track wall 112, as can be seen in FIG. 8. The tab 136 is pressed downward into the socket 134 and a tool (not shown) is inserted through an opening 144 in the base of the tray 102 to cause the tab 136 to bend to form a generally U-shaped cleat, as shown in FIG. 12. The wall 140 has a lip 146 at its upper end extending into the socket 134. The free end of the tab 136 resiliently abuts the underside of the lip 146 to provide a secure attachment of the lid 120 to the tray 102. Four such points of attachment for the lid are preferred, but three would be adequate and are used on a small version (not shown) of the suture packet.

Figure 13:
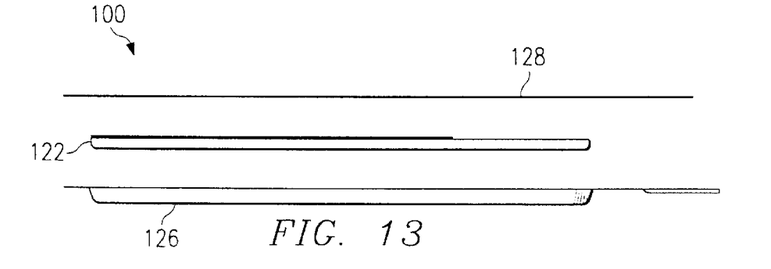
FIG. 13 is an exploded side view of the surgical suture package of the present invention.
Figure 14:
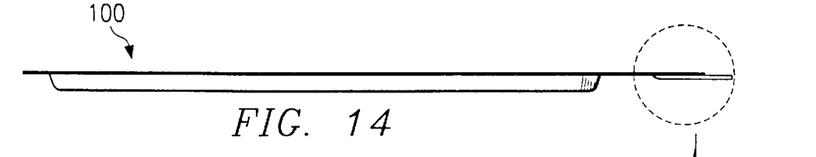
FIG. 14 is a side view of a sealed surgical suture package of the present invention.
Figure 16:
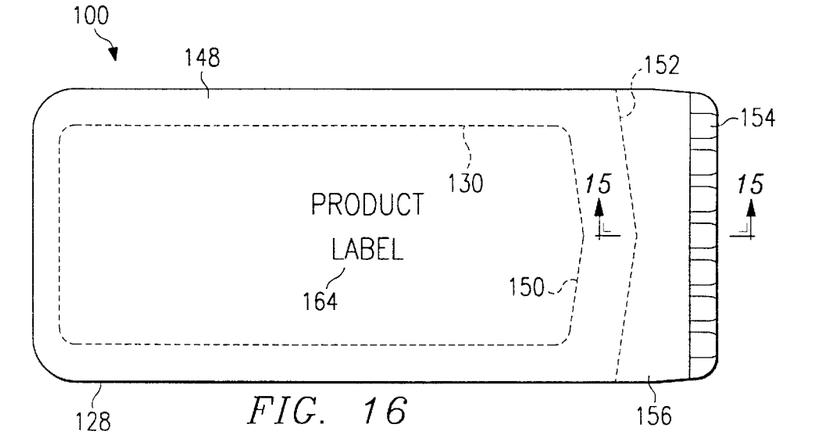
FIG. 16 is a top plan view of the package of the present invention.
Figure 17:
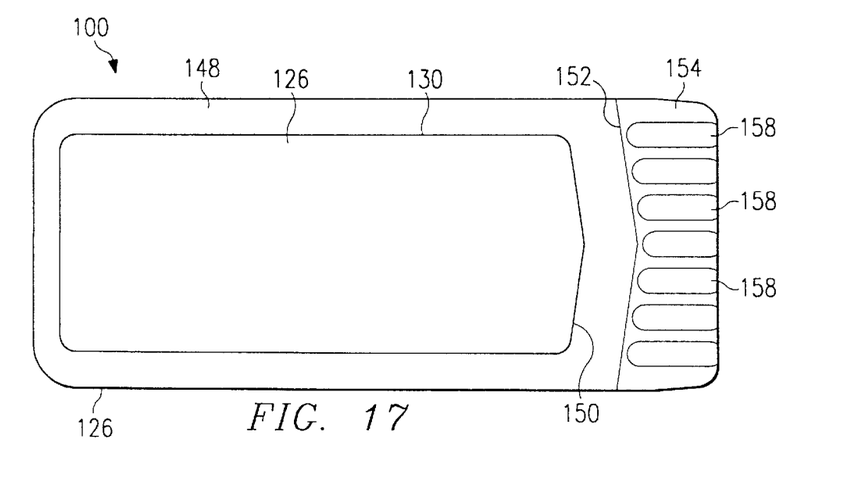
FIG. 17 is a bottom plan view of the package of the present invention.

With the needle-suture assembly 104, 106 disposed in the tray 102 and the lid 120 attached using the tabs 136 deformed as U-shaped cleats, the packet 122 is placed in the cavity of the bottom foil 126 and the top foil 128 is placed atop the bottom foil 126. The package 100 is shown in exploded side view in FIG. 13 and in its assembled form in FIG. 14. After processing through the sterilization procedure, the peripheral seal is formed and the package 100 is ready for shipment. FIGS. 16 and 17 show the package in top and bottom plan views in its final sealed condition.

In the preferred embodiment of the improved surgical suture package 100 of the present invention, a peripheral heat seal is provided around the cavity 130 within which the suture packet 122 is retained. The location of the peripheral seal is denoted by reference numeral 148 in FIGS. 16 and 17 and corresponds to the area of the peripheral flange 132 seen in FIG. 8.

The preferred shape of the cavity 130 is seen in FIGS. 8, 16 and 17, and has an apex-shaped front edge 150. The portion of the peripheral seal adjacent to the front edge 150 of the cavity 130 has a similar apex or chevron shape and includes a pointed leading edge 152. To the right of the seal in the orientation of FIGS. 16 and 17 are unsealed flaps, reference numeral 154 designating the bottom foil flap and reference numeral 156 designating the top foil flap. As seen in FIG. 16, the bottom flap 154 extends slightly beyond the end of the top flap 156. This facilitates grasping the flaps with one's fingers and pulling them apart to open the package 100.

A plurality of ribs 158 are provided in the bottom flap 154, seven such ribs being provided in the preferred embodiment in the manner shown in FIG. 17. The ribs 158 are parallel and oriented longitudinally to add stiffness to the flap 154. Since the bottom flap 154 extends beyond the end of the top flap 156, the bottom flap 154 is vulnerable to bending or crumpling due to inadvertent contact in handling during the manufacturing procedure. The ribs 158 tend to resist such bending or crumpling of the bottom flap 154. The ribs 158 preferably comprise depressions formed by a die (not shown) during the same operation that forms the cavity 130 in the bottom foil 126.

The bottom flap 154 preferably has rounded corners to facilitate loading of packages 100 into shipping cartons (not shown). The corners of the package 100 opposite the flap end also are preferably rounded to facilitate loading into shipping cartons, though such corners are relatively stiff because they are in the seal area where the two foils are fused together.

Figure 15:
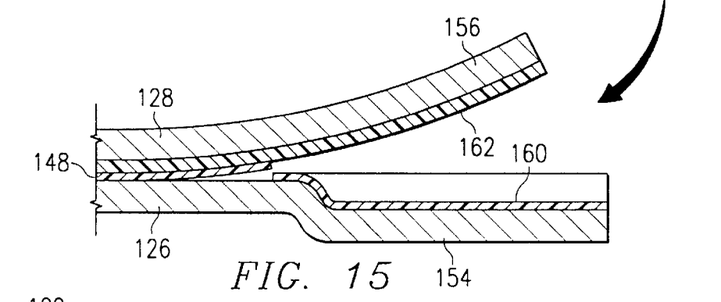
FIG. 15 is a schematic cross section of flaps at the end of the package of FIG. 14 illustrating the flaps being pulled apart, the thickness dimensions of the elements being exaggerated and not to scale.

With reference to FIG. 15, the preferred heat-sensitive coatings will be described. FIG. 15 shows a cross section through the flaps 154 and 156 just after they have been pulled apart sufficiently to begin breaking the seal. The bottom foil 126 has a thin polymeric coating 160 on its upper surface, and the top foil 128 has a relatively thick polymeric coating 162 on its bottom surface.

The thin heat seal coating 160 preferably comprises a polypropylene material, and the relatively thick coating 162 preferably comprises a polypropylene copolymer material. Such materials are sold under the "Morprime" trademark by the Morton Chemical Division of Morton Thiokol, Inc. Aluminum foils coated with such materials may be purchased from the American Can Company. Such aluminum foils may be purchased in 18 inch diameter rolls. A roll of top foil stock preferably measures 9.875 inches in width, which is then cut into sheets preferably 10.250 inches in length. A roll of bottom foil stock preferably measures 10.875 inches in width, which is then cut into sheets preferably 10.000 inches in length. In processing, the top sheets are reoriented 90° so that the top foil dimension of 10.250 inches is aligned with the bottom foil dimension of 10.875 inches. One half of the difference in these dimensions determines the amount by which the bottom flap 154 extends beyond the top flap 156 in the final package 100, which is approximately 0.3125 inch.

The polypropylene copolymer on the top foil 128 is preferably applied in the amount of 10 pounds per ream (a ream being a standard measure of area). The polypropylene on the bottom foil 126 is preferably applied in the amount of 1.4 pounds per ream. These amounts determine the approximate thicknesses of the coatings 160 and 162.

In the sealing operation, the coatings 160 and 162 are fused together to form a moisture impervious seal 148 surrounding the cavity 130. At the beginning of the sterilization procedure, a "primary" seal is formed to provide a U-shaped seal (not shown) around the end of the cavity opposite the flaps 154 and 156. In the preferred procedure, the packages are processed through sterilization in frames of eight packages, arranged two by four. The U-shaped seals form an interdigitated pattern (not shown) with fingers extending between adjacent cavities. The die which forms the primary seal is preferably maintained at a temperature of 196° C.±6° C., and applied at a pressure of 60 bar±5 bar, for 1.2±0.1 seconds. After the sterilization procedure, a "secondary" seal is formed in a U-shaped pattern (not shown) at the chevron-shaped end of the cavity and extending along the sides of the cavity to overlap the primary seal previously formed. These two sealing operations complete the formation of the entire peripheral seal 148. Again, the secondary seal is preferably effected on the frame of eight packages so that two interdigitated patterns (not shown) of five fingers each are applied to the frame. The die which forms the secondary seal is preferably maintained at a temperature of 194° C.±5° C., and applied at a pressure of 45 psi±5 psi, for 1.3±0.1 seconds.

The fused seal 148 at the interface of the two polymeric coatings 160 and 162 is stronger than the bonds between the coatings and the respective foils 126 and 128. Also, the adhesive bond between the thicker coating 162 and the bottom surface of the top foil 128 is stronger than the adhesive bond between the thinner coating 160 and the top surface of the bottom foil 126.

When the user opens the package 100 by pulling apart the flaps 154 and 156 as shown in FIG. 15, the coatings 160 and 162 remain fused together in the seal area, such that the coating 160 peels away from the top surface of the bottom foil 126. The force required to initiate such peeling is minimized by the apex shape of the leading edge 152 of the seal 148. Furthermore, as the peeling operation continues, the moving line of separation of the coating 160 from the bottom foil 126 reaches the cavity and first encounters the point of the apex-shaped front end of the cavity 130. Thus, the force required to continue the peeling operation into the cavity area diminishes gradually rather than abruptly, further facilitating the opening of the package 100.

Another feature of the preferred embodiment of the invention is the provision of product label indicia 164 on a specially coated top surface of the top foil 128. A thin polyester film is first applied to the top surface of the top foil 128. A titanium dioxide finish is then applied to the polyester film to provide a coating with a matte finish, which facilitates printing of product label indicia thereon, as indicated by reference numeral 164 in FIG. 16.

From the foregoing, it will be appreciated that the improved package 100 of the present invention has a number of advantages over the prior art package 10. Most notably, the improved package 100 eliminates the redundantly sealed double layers of packaging, with resulting efficiencies for manufacturing and use. The peelable foil seal 148 is easy to open to gain access to the sterile suture product contained within the package 100. The needle 104 is readily accessible using forceps, without the need to remove any portion of the paper lid 120 from the plastic tray 102. Because the improved package 100 can accommodate a larger suture packet than the prior art package 10, a simplified needle mounting arrangement can be provided in the tray 102 so that different size needles can be secured in the same location. Other advantages of the improved package 100 will be apparent from the foregoing description.

Although a preferred embodiment of the present invention has been described in detail, it will be appreciated that various alternatives and modifications thereof are within the spirit and scope of the invention as set forth in the appended claims.

What is claimed is:

1. A package for surgical sutures, comprising:
a packet for retaining a needle-suture assembly; and
a container having first and second foils, the foils having heat-sensitive polymeric coatings adhered to their inner surfaces, one of the foils having a cavity for receiving the packet, the heat-sensitive coatings having thermally fused portions surrounding the cavity to define a peripheral seal which maintains the packet within the cavity in a sterile condition, each foil having a flap at one end of the container extending beyond the peripheral seal, one flap being longer and extending beyond the end of the other flap, the longer flap having stiffness-adding ribs disposed in the portion extending beyond the end of the other flap, the flaps enabling the foils to be peeled apart to break the seal and permit access to the packet, the polymeric coating on the first foil being thicker than the polymeric coating on the second foil such that the thinner coating stays fused to the thicker coating and peels away from the second foil as the flaps are pulled apart breaking the seal.

2. The package of claim 1 wherein the foils consist essentially of aluminum, and the two polymeric coatings are of different compositions such that the adhesive bond between the thicker coating and the inner surface of the first foil is stronger than the adhesive bond between the thinner coating and the inner surface of the second foil.

3. The package of claim 2 wherein the peripheral seal defines an apex shape in the area between the cavity and the flaps, whereby the point of the apex is peeled apart first as the flaps are pulled apart to break the seal, thus initiating the peeling process with minimum force.

4. A package for surgical sutures, comprising:
an elongated packet for retaining a needle-suture assembly the packet including a tray having a plurality of sockets, and a lid covering a portion of the tray, the lid having tabs located to correspond to sockets in the tray, each tab extending into a corresponding socket and engaging a portion of an interior surface of the socket to assist in securing the lid to the tray, each socket having an internal lip, and each tab being deformed to define a generally U-shaped cleat with its free end abutting the underside of the corresponding lip; and a container having top and bottom metal foils, a first polymeric coating adhered to the bottom surface of the top foil, a second polymeric coating adhered to the top surface of the bottom foil, the bottom foil having an elongated cavity for receiving the packet, the coatings having thermally fused portions surrounding the cavity to define a peripheral seal which maintains the packet within the cavity in a sterile condition, each foil having a flap at one end of the container extending beyond the peripheral seal, the bottom foil flap extending longitudinally slightly beyond the end of the top foil flap to ease opening of the package, the flaps enabling the foils to be peeled apart to break the seal and permit access to the packet, the adhesive bond between the first polymeric coating and the bottom surface of the top foil being stronger than the adhesive bond between the second polymeric coating and the top surface of the bottom foil, such that the second coating stays fused to the first coating and peels away from the bottom foil as the flaps are pulled apart breaking the seal.

5. The package of claim 4 wherein the bottom flap extends beyond the end of the top flap by about 5/16 of an inch.

6. The package of claim 4 further comprising a plurality of parallel ribs disposed longitudinally in the bottom flap to resist bending, the ribs comprising depressions formed in the bottom foil during the formation of the elongated cavity.

7. The package of claim 4 wherein the cavity has an apex shape at the end adjacent to the flaps, and the peripheral seal has a conforming apex shape between the apex-shaped end of the cavity and the flaps, whereby peeling apart of the foils to break the seal and access the packet is facilitated.

8. The package of claim 4 wherein the packet includes a generally oval-shaped plastic tray, the tray having a substantially flat base, an outer wall extending generally upward around the periphery of the base, an inner wall spaced inwardly from the outer wall and extending generally upward from the base, and a plurality of teeth adjoining the upper edge of the inner wall and extending outward to points proximate to the outer wall, wherein the walls define a peripheral track for retaining a suture, and wherein the teeth are flexible and resiliently return to a plane parallel to the base, whereby in the manufacturing procedure the teeth are bent upwards as the suture is loaded into the track in a coiled arrangement and then are allowed to resiliently return to their ordinary position in the parallel plane to retain the suture within the track.

9. The package of claim 4 wherein the tray includes slotted rib elements for mounting a needle in the tray, and walls defining a peripheral track for retaining a suture in a coiled arrangement in the tray.

10. The package of claim 9 wherein the lid covers a major portion of the tray including the portion in which the point of the needle resides, and does not cover the portion of the tray which includes the end of the needle to which the suture is attached, whereby the lid does not inhibit removal of the needle-suture assembly from the tray.

11. The package of claim 4 wherein the top foil includes a titanium dioxide finish on its top surface, and product label indicia is printed on the titanium dioxide finish.

12. A package for surgical sutures, comprising:
an elongated plastic tray having a substantially flat base, slotted ribs disposed on an upper surface of the base for retaining a needle in place in the tray, an outer wall extending generally upward around the periphery of the base, an inner wall spaced inwardly from the outer wall and extending generally upward from the upper surface of the base, the walls defining a track for retaining a suture, a plurality of sockets extending upward from the base, each socket having first and second facing walls defining an opening, the first wall including a lip overhanging the opening above the upper surface of the base;

a flat lid for covering a substantial portion of the plastic tray including the portion within which the point of the needle resides, the lid comprising a relatively stiff paper material, the lid having tabs located to correspond to the sockets in the plastic tray, each tab being defined by a three-sided cutout such that the fourth side of the tab is hingedly secured to the major portion of the lid, each tab being deformable to define a generally U-shaped cleat with its free end abutting the underside of the lip in the corresponding socket of the plastic tray;

a bottom metal foil having an elongated cavity for receiving the plastic tray, a flange extending outward in a plane from the periphery of the cavity, the flange having a flap extending from one end of the foil in the longitudinal dimension of the cavity;

a top metal foil corresponding generally to the shape of the bottom metal foil and having a flap extending longitudinally in the same direction as the flap on the bottom metal foil, the bottom flap having an edge extending beyond the end of the top flap to facilitate bending the bottom flap away from the top flap when opening the package;

heat sensitive coatings on the facing surfaces of the foils, the coatings being differentiated to facilitate peeling open the package; and a seal formed by selective heating of the heat sensitive coatings around the cavity, the seal defining an apex shape in the area between the cavity and the flaps to reduce the force required to peel apart the flaps when opening the package.

13. The package of claim 12 further comprising:

a coating on the top surface of the top metal foil, the coating including a polyester film in contact with the top surface of the top foil and a titanium dioxide finish atop the polyester film; and product label indicia printed on the titanium dioxide finish.

14. The package of claim 12 wherein the bottom flap includes a plurality of parallel ribs formed therein and extending longitudinally between the seal and the end of the flap.

15. The package of claim 14 where in the bottom flap further includes rounded corners.

16. In a package for containing surgical sutures in a sterile condition, the container comprising:

first and second adjacent aluminum foils;

a first polymeric coating on the bottom surface of the first foil;

a second polymeric coating on the top surface of the second foil;

a seal defining a cavity between the foils, the seal comprising thermally fused portions of the coatings; and unsealed flaps extending from the ends of the foils to facilitate pulling the foils apart to break the seal and access the cavity, one flap being longer and including stiffness-adding ribs disposed in the portion extending beyond the end of the other flap;

wherein the coatings are differentiated such that one of the coatings peels away from its foil as the seal is broken.

17. The package of claim 16 wherein the ribs comprise parallel elongated depressions formed in the longer flap.

18. The package container of claim 17 wherein the first polymeric coating consists essentially of a polypropylene copolymer, and the second polymeric coating consists essentially of a polypropylene.

19. The package container of claim 18 wherein the first polymeric coating is much thicker than the second polymeric coating.

20. The package container of claim 16 wherein the container is generally rectangular having a width of about 2¼ inches and a length of about 5⅛ inches.

* * * * *

UNITED STATES PATENT AND TRADEMARK OFFICE
CERTIFICATE OF CORRECTION

PATENT NO. : 5,833,055
DATED : November 10, 1998
INVENTOR(S) : Robert J. Cerwin; Clifford A. Dey; John M. Findlay; Konstantin K. Ivanov; Robert Nunez; Donald Pompei; William R. Reinhardt; Mehmet Reyhan; David A. Szabo It is certified that error appears in the above-indentified patent and that said Letters Patent is hereby corrected as shown below:

TITLE PAGE

[73] Assignee: Summerville SHOULD BE Somerville

Signed and Sealed this

Twenty-sixth Day of October, 1999

Attest:

Q. TODD DICKINSON

Attesting Officer     Acting Commissioner of Patents and Trademarks